United States Patent
Döring et al.

(10) Patent No.: US 10,611,717 B2
(45) Date of Patent: Apr. 7, 2020

(54) PROCESS FOR THE COUPLED PRODUCTION OF SWEET WHEY AND LACTIC ACID FROM ACID WHEY

(71) Applicant: DMK Deutsches Milchkontor GmbH, Zeven (DE)

(72) Inventors: Sven-Rainer Döring, Zeven (DE); Mareike Hunold, Zeven (DE)

(73) Assignee: DMK Deutsches Milchkontor GmbH, Zeven (DE)

( * ) Notice: Subject to any disclaimer, the term of this patent is extended or adjusted under 35 U.S.C. 154(b) by 120 days.

(21) Appl. No.: 15/868,000

(22) Filed: Jan. 11, 2018

(65) Prior Publication Data

US 2018/0208535 A1    Jul. 26, 2018

(30) Foreign Application Priority Data

Jan. 22, 2017  (EP) ..................... 17152543

(51) Int. Cl.
*C07C 51/47*    (2006.01)
*A23C 9/142*    (2006.01)
(Continued)

(52) U.S. Cl.
CPC ............... *C07C 51/47* (2013.01); *A23C 1/04* (2013.01); *A23C 9/1425* (2013.01);
(Continued)

(58) Field of Classification Search
CPC ..... C07C 51/47; A23C 9/1425; A23C 9/1427; A23C 21/10; A23C 21/026; A23J 1/205
(Continued)

(56) References Cited

U.S. PATENT DOCUMENTS

2012/0121781 A1*  1/2012  Scott et al.
2014/0348981 A1   11/2014  Smith et al.

FOREIGN PATENT DOCUMENTS

CN    101648898    *  2/2010
GB    2293825 A        4/1996
WO    2014163486 A1   10/2014

OTHER PUBLICATIONS

Mezzonifoods, "Dry Lactic Acid Powder", 2013, https://www.mezzonifoods.com/buy-dry-lactic-acid-powder, pp. 1-2. (Year: 2013).*

(Continued)

*Primary Examiner* — Helen F Heggestad
(74) *Attorney, Agent, or Firm* — Dilworth & Barrese, LLP

(57) ABSTRACT

A process for the coupled production of sweet whey and lactic acid from acid whey is suggested, comprising the following steps:
(a) providing acid whey having a lactic acid content of about 0.1 to about 1% by weight;
(b) nanofiltration of the acid whey, obtaining a first permeate P1 and a first retentate R1;
(c) optionally, redilution of the first retentate R1 with water to reconstitute the initial dry matter content, and preparation of the second nanofiltration step;
(d) nanofiltration or nano-diafiltration of the retentate R1, obtaining a second permeate P2 and sweet whey as a second retentate R2;
(e) combining the two permeates P1 and P2 and subjecting the mixture to reverse osmosis, obtaining a third permeate P3 which, substantially, only contains water, and a concentrate of lactic acid as a third retentate R3.

8 Claims, 1 Drawing Sheet

(51) Int. Cl.
  B01D 61/02    (2006.01)
  A23J 1/20     (2006.01)
  A23C 1/04     (2006.01)
  A23C 21/02    (2006.01)
  A23J 1/08     (2006.01)
  A23C 21/00    (2006.01)
  C07K 14/47    (2006.01)
  C07K 1/34     (2006.01)

(52) U.S. Cl.
  CPC ............ *A23C 9/1427* (2013.01); *A23C 21/00* (2013.01); *A23C 21/026* (2013.01); *A23J 1/08* (2013.01); *A23J 1/205* (2013.01); *B01D 61/022* (2013.01); *A23C 2210/206* (2013.01); *A23V 2002/00* (2013.01); *B01D 61/025* (2013.01); *B01D 61/027* (2013.01); *B01D 2315/16* (2013.01); *C07K 1/34* (2013.01); *C07K 14/47* (2013.01)

(58) Field of Classification Search
  USPC ........................................ 426/583, 491, 520
  See application file for complete search history.

(56) References Cited

OTHER PUBLICATIONS

WayBack Machine for Mezzonifoods reference above, showing date of Aug. 18, 2013, pp. 1-2, https://web.archive.org/web/2018*https://www.mezzonifoods.com/buy-dry-lactic-acid-pow . . . (Year: 2019).*
Barrantes et al., "Partial Deacidification and Demineralization of Cottage Cheese Whey by Nanofiltration," Journal of Food Science, 62(2): Mar. 1, 1997, pp. 338-341.
Li et al., "Separate and Concentrate Lactic Acid Using Combination of Nanofiltration and Reverse Osmosis Membranes," Appl Biochem Biotechnol 147: Sep. 25, 2007, pp. 1-9.
Román et al., "Partial demineralization and concentration of acid whey by nanofiltration combined with diafiltration," Desalination, Elsevier, 241: 2009, pp. 288-295.
Timmer et al., "Transport of lactic acid through reverse osmosis and nanofiltration membranes," Journal of Membrane Science, 85(2): Nov. 11, 1993, pp. 205-216.
González et al., "Lactic acid recovery from whey ultrafiltrate fermentation broths and artificial solutions by nanofiltration," Desalination:, Elsevier, 228: 2008, pp. 84-96.
Chandrapala et al.; "Strategies for maximizing removal of lactic acid from acid whey—Addressing the unprocessability issue," Separation and Purification Technology, Elsevier Science, 172(6): Sep. 6, 2016, pp. 489-497.
Chandrapala et al., "Nanofiltration and nanodiafiltration acid whey as a function of pH and temperature," Separation and Purification Technology, Elsevier Science, 160(29): Dec. 29, 2015, pp. 18-27.
Pan et al., "A study of demineralization of whey by nanofiltration membrane," Desalination, Elsevier, 267: Feb. 15, 2011, pp. 217-221.
Jindal et al., "Preparation and Composition of Chhana Whey Powders Using Membrane Processing Techniques," Journal of the Science of Food and Agriculture, 58(4): Jan. 1, 1992, pp. 511-517.
Timmer et al., "Lactic acid separation from fermentation broths by reverse osmosis and nanofiltration," Journal of Membrane Science, Elsevier 92: Jan. 1. 1994, pp. 185-197.
Nguyen et al., "By-product recovery from cottage cheese production by nanofiltration," Journal of Cleaner Production 11(7): Nov. 1, 2003, pp. 803-807.
Bogdan et al., "Characteristics of Acid Whey Powder Partially Demineralised by Nanofiltration", Polish Journal of Food and Nutrition Sciences 15(56), Jan. 1, 2006, pp. 87-90.

\* cited by examiner

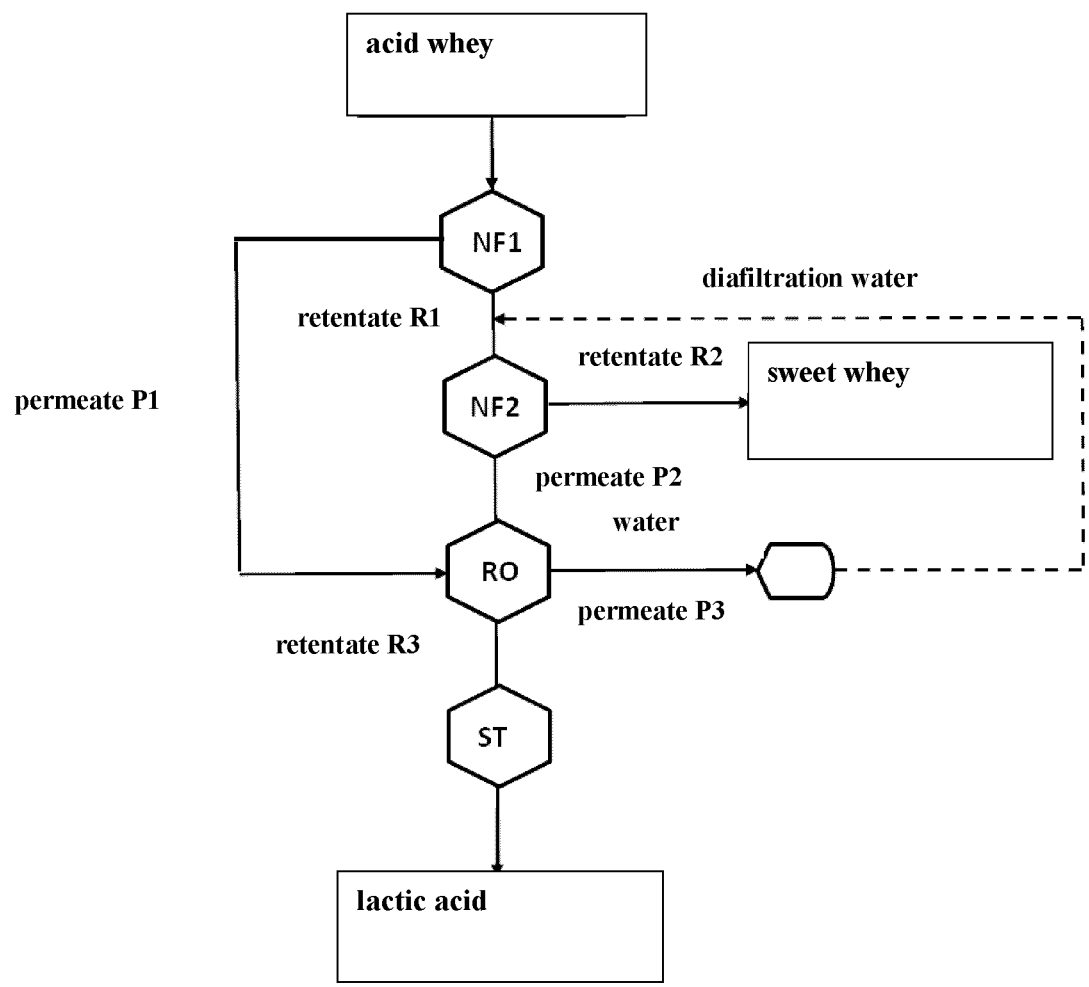

PROCESS FOR THE COUPLED PRODUCTION OF SWEET WHEY AND LACTIC ACID FROM ACID WHEY

FIELD OF THE INVENTION

The invention is in the field of dairy processing and relates to a process by means of which it is possible to convert acid whey into sweet whey, obtaining lactic acid as a valuable coupled product in the process.

STATE OF THE ART

Whey is the aqueous greenish-yellowish fluid left over from the process of cheese making. It is the liquid portion, which is separated after the curdling of milk to produce cheese or quark. There are two types of whey, which are distinguished depending on the production process: sweet whey is formed during the coagulation of milk by means of rennet for the production of cheese, and acid whey is formed during the fermentation of milk by lactic acid bacteria. Whey has 94% by weight water, 4 to 5% by weight lactose and is virtually fat-free. It also contains lactic acid, vitamins B1, B2 (which are causing the greenish colour) and B6 as well as potassium, calcium, phosphorus and other minerals, but primarily 0.6 to 1% by weight whey protein. As a consequence, whey contains significantly less protein than milk. In particular, in contrast to milk, it does not contain any casein. Sweet whey has an almost neutral pH, while acid whey, in contrast, has a pH value of 5 or less.

Sweet whey is considered to be the most important form of whey, serving as a source of raw material for other dairy products, especially of the so-called whey proteins, but it is also used in the food sector.

In contrast, acid whey is a waste product that is obtained in great quantities during the production of fresh cheese and of quark. As a result of the high lactic acid content and its associated low pH value, it can only be used with restrictions for human nutrition. Acid whey is also difficult to filter, and only with great difficulty can it be spray-dried. As a result, this side product of the production of cheese is usually disposed of, leading to additional environmental pollution and costs; this also constitutes a loss, as ingredients of the milk are lost in this process, which are interesting per se, particularly whey proteins, lactose and calcium phosphate.

The object of the invention was, therefore, to remove any undesired constituents of acid whey such that a commercially attractive and exploitable product is obtained. In particular, a product was required which is almost identical to sweet whey with respect to its composition and pH value, providing lactic acid as an attractive industrial raw material as a coupled product in a form that is concentrated as highly as possible, and which is as pure as possible.

DESCRIPTION OF THE INVENTION

The subject matter of the invention relates to a process for the coupled production of sweet whey and lactic acid from acid whey, comprising the following steps:
(a) providing acid whey having a lactic acid content of about 0.1 to about 1% by weight;
(b) nanofiltration of the acid whey, obtaining a first permeate P1 and a first retentate R1;
(c) optionally, redilution of the first retentate R1 with water to reconstitute the initial dry matter content, and preparation of the second nanofiltration step;
(d) nanofiltration of the retentate R1, obtaining a second permeate P2 and sweet whey as a second retentate R2;
(e) combining the two permeates P1 and P2 and subjecting the mixture to reverse osmosis, obtaining a third permeate P3 which, substantially, only contains water, and a concentrate of lactic acid as a third retentate R3.

Surprisingly, it was found that by a two-step nanofiltration process it was possible to convert acid whey into a product having the quality of sweet whey, whereby lactic acid in industrial grade purity is obtainable as a coupled product. The desired depletion in lactic acid and, naturally, also in the amount of the desired coupled product of the whey can be controlled selectively by selecting suitable membranes and filtration conditions. Within the scope of the process of the invention, a simultaneous partial demineralisation of the raw materials is also taking place. The degree of demineralisation is between 50 and 70%. The salt content is transferred to the lactic acid solution.

BRIEF DESCRIPTION OF THE DRAWING

The invention will be described in greater detail with reference to the accompanying FIGURE which schematically illustrates a flowchart of the process according to the present invention.

ACID WHEY

As explained above, acid whey constitutes the liquid phase, which is produced in the process of coagulating milk to produce fresh cheese or quark using lactic acid bacteria. Preferably, qualities are used which have a lactic acid content in the range of about 0.1 to 1% by weight.

Nanofiltration

Nanofiltration is a filtration process from the field of membrane technology, by means of which macro-molecular substances and small particles may be separated from a medium and concentrated. The degree of separation is decisive for the difference between macrofiltration, ultrafiltration and nanofiltration. If the cut-off limit (or also "cut-off") is 100 nm or more, it is referred to microfiltration. If the cut-off limit is in the range between 2-100 nm, this is referred to as ultrafiltration. In the case of nanofiltration, the cut-off limit is below 2 nm. In each of these cases, this concerns purely physical, i.e. mechanical membrane separation methods which apply the principle of mechanical size exclusion: all particles in the fluids which are larger than the membrane pores are retained by the membrane. The driving force in both separation methods is the differential pressure between the inlet and the outlet of the filter area, which is between 1 and 40 bar, in some cases up to 120 bar.

The cut-off limits of nanofiltration membranes are also indicated in form of the NMWC (Nominal Molecular Weight Cut-Off, also referred to as MWCO, Molecular Weight Cut Off, unit: Dalton). It is defined as the minimal molecular mass of more global molecules, 90% of which are retained by the membrane. In practice, the NMWC should be at least 20% lower than the molecular mass of the molecule to be separated. Further qualitative statements on filtration may be made by means of the flux (water value) (transmembrane flux or passage rate). Ideally, it is proportional to the transmembrane pressure and reciprocal to the membrane resistance. These sizes are determined both by the characteristics of the membrane used and by concentration polarisation and possibly occurring fouling. The passage rate relates to 1 $m^2$ of membrane area. Its unit is $l/(m^2 \cdot h \cdot bar)$.

With respect to a possibly efficient separation of lactic acid in two steps, it has shown to be advantageous to perform the second nanofiltration step using a membrane which has a greater cut-off than the membrane of the first nanofiltration step.

Specifically, it is recommended to perform the first nanofiltration step using an open membrane, preferably one having a cut-off in the range of about 500 to about 1,000 Dalton, and particularly of about 800 Dalton. It is also preferred to perform the nanofiltration process at a pressure in the range of about 10 to about 15 bar. In applying these combined conditions, a retentate can be obtained which only has about 20% of the originally obtained lactic acid. If closed membranes with a higher cut-off and/or higher or lower pressures are used, only between about 25 and about 50% by weight of lactic acid are removed instead of 80, leading to the result that the second nanofiltration step will be initiated with a higher lactic acid content, achieving a correspondingly comparably lower separation performance.

Before performing the second nanofiltration step, it is recommended to add to retentate 1 the amount of water which was previously removed together with permeate 1. This avoids that the osmotic pressure increases too much at this point, and also, that the filtration/purification performance is insufficient. The amount of lactic acid within retentate 2 can be controlled by means of the quantity of diafiltration water.

Preferably, the second nanofiltration step is subsequently performed using a closed membrane, which, particularly, has a cut-off in the range of about 150 to about 300 Dalton. In this case, it is recommended to operate at a higher pressure in the range of about 30 to about 40 bar. Depending on the concentration of lactic acid in the applied retentate from the first nanofiltration, retentates are obtained from the second step which contain between 0.1 and 0.5% by weight residual lactic acid, thus practically corresponding to sweet whey, or at least getting close to it.

The material of the nanofiltration membrane may represent stainless steel, polymer materials, ceramics, aluminium oxide or textile fabric. Filter elements appear in different forms: candle filters, flat membranes, spiral coil membranes, bag filters and hollow fibre modules, all of which are, in principle, suitable within the meaning of the present invention. However, spiral coil membranes made of polymer materials or candle filters made of ceramics or aluminium oxide are preferably used, where the second form of embodiment has proved to be particularly preferred for nanofiltration.

Both nanofiltration steps within the meaning of the present invention may be performed "hot" or "cold", i.e., within the temperature range of about 10 to about 60° C. However, it is preferred to operate at temperatures in the range from 10 to about 20° C.

Reverse Osmosis

Reverse osmosis is a physical membrane process for the concentration of substances dissolved in liquids, in the process of which the natural osmotic process is reversed by means of pressure. In the present case, this step serves to concentrate the mixture of the two permeates P1 and P2 in order to have less water removed in the following drying step.

The principle of the process is that the medium in which the concentration of a particular substance is to be reduced is separated by a semi-permeable membrane from the medium in which the concentration is to be increased. The latter is subjected to a pressure which must be higher than the pressure created by the osmotic pressure for concentration equilibration. As a result of this, the molecules of the solvent can migrate in opposite direction to their "natural" osmotic spreading direction. The pressure forces them into the compartment in which dissolved substances are present in a less concentrated form. Typical pressures of reverse osmosis are in the range from 3 to 30 bar (desalination of drinking water) or up to 80 bar (desalination of sea water).

The osmotic membrane through which only the carrier liquid (solvent) is allowed to pass, retaining the dissolved substances (solute), must be able to withstand these high pressures. In case the pressure difference more than balances the osmotic gradient, the molecules of the solvent are passing through the membrane just like in a filter, while the "contaminating molecules" are retained. In contrast to a classic membrane filter, osmotic membranes do not have through pores. The ions and molecules rather migrate through the membrane by diffusing through the membrane material, as is described by the solution-diffusion model: the osmotic pressure increases with an increasing concentration difference. If the osmotic pressure becomes equal to the applied pressure, the process ceases. An osmotic equilibrium is present. A continuous discharge of concentrate may prevent this from occurring. During the discharge of concentrate, the pressure is either controlled by means of a pressure controller or used by means of a pressure exchanger to accumulate the pressure required at the inflow of the system.

Drying

Ultimately, the lactic acid concentrates obtained by means of reverse osmosis as retentates can be dehydrated. Preferably, spray-drying is applied, whereby the temperature at the inlet typically is about 180 to about 260° C., and about 80 to about 105° C. at the outlet. As a result, the fraction does not need any cooling before entering the tower. Temperatures of 60 to 70° C. are even preferred in this process, as this reduces the risk of denaturation of the proteins. Alternatively, the products may also be dehydrated by freeze drying. The yield, based on the lactic acid contained in the original acid whey, is about 70 to 90% with a purity of 90 to 95%.

The invention is illustrated below by examples of embodiment and by FIG. 1, which provides a flowchart of the process that does not intend to restrict it.

EXAMPLES

Example 1

100 kg acid whey having a lactic acid content of 0.45% by weight and a pH value of 4.9 was supplied to a nanofiltration step at a flow rate of 5 kg/min where it was filtered through an open membrane having a cut-off of 800 Dalton at a temperature of 20° C. and a pressure of 12 bar as well as a volume concentration factor (VCF) of 4.75 kg of the first permeate P1 was obtained, which had 0.365% by weight lactic acid, and 25 kg of the retentate R1, which still contained 0.7% by weight lactic acid. Thus, 80% of the original amount of lactic acid were detected in the permeate. 75 kg water were added to the first retentate and then supplied to a further nanofiltration step where it was filtered through a closed membrane with a cut-off of 200 Dalton at a temperature of 20° C. and a pressure of 35 bar. A second permeate P2 was obtained having 0.18% by weight lactic acid, while the second retentate R2 was depleted to 0.2% by weight lactic acid, thus having the quality of sweet whey.

Example 2

100 kg acid whey having a lactic acid content of 0.45% by weight and a pH value of 4.9 was supplied to a nanofiltration step at a flow rate of 5 kg/min where it was filtered through an open membrane having a cut-off of 800 Dalton at a temperature of 20° C., a volume concentration factor of 4 and a pressure of 35 bar. A first permeate P1 was obtained, which had 0.23% by weight lactic acid, and a first retentate R1, which contained 1.1% by weight lactic acid. Thus, in this example only 50% of the original amount of lactic acid were detected in the permeate. 75 kg water (P3) was added to the first retentate and subsequently supplied to a further nanofiltration step where it was filtered through a closed membrane having a cut-off of 200 Dalton, at a temperature of 20° C. and a pressure of 35 bar. A second permeate P2 was obtained, which had 0.05% by weight lactic acid while the second retentate R2 was depleted up to 0.95% by weight lactic acid in the concentrate, which approximately corresponds to about 0.27% by weight lactic acid in the initial solution, thus having a similar quality as sweet whey.

Example 3

100 kg acid whey having a lactic acid content of 0.45% by weight and a pH value of 4.9 was supplied to a nanofiltration step at a flow rate of 5 kg/min where it was filtered through an open membrane having a cut-off of 200 Dalton at a temperature of 20° C., a VCF of 4 and a pressure of 35 bar. 75 kg of the first permeate P1 was obtained, which had 0.11% by weight lactic acid, and 25 kg of the first retentate R1 which still contained 1.47% by weight lactic acid. Thus, in this example, only 25% of the original amount of lactic acid were detected in the permeate. 75 kg water (P3) was added to the first retentate and supplied to a further nanofiltration step where it was filtered through a closed membrane having a cut-off of 200 Dalton, at a temperature of 20° C. and a pressure of 35 bar. A second permeate P2 was obtained, having 0.09% by weight lactic acid, while the second retentate R2 had 1.2% by weight lactic acid in the concentrate, which corresponds to 0.3% by weight in the initial concentration. In doing so, a similar quality of sweet whey could be achieved to a limited extent.

Example 4

The first and second permeates of examples 1 to 3 were supplied to a reverse osmosis unit where they were concentrated up to a residual water content of 25% by weight. Subsequently, the concentrates were pre-heated to 90° C. using a heat exchanger, applied to a tower and spray-dried at 180° C. Lactic acid was obtained as a fine white crystal powder in a purity of about 85%. About 10-20% of the dry matter is formed by the mineral salts from the acid whey. As a result of the low pH value of the acid whey, these salts are also permeable at the nanofiltration membrane.

The invention claimed is:

1. A process for the coupled production of sweet whey and lactic acid from acid whey, comprising the following steps:
   (a) providing acid whey having a lactic acid content of about 0.1 to about 1% by weight;
   (b) nanofiltration of the acid whey using an open nanofiltration membrane having a cut-off in the range of about 500 to about 2,000 Dalton, obtaining a lactic acid rich first permeate P1 and a first retentate R1;
   (c) optionally, redilution of the first retentate R1 with water to reconstitute the initial dry matter content, and preparation of the second nanofiltration step;
   (d) nanofiltration or nano-diafiltration of the retentate R1, obtaining a lactic acid rich second permeate P2 and sweet whey as a second retentate R2; and
   (e) combining the two permeates P1 and P2 and subjecting the mixture to reverse osmosis, obtaining a third permeate P3 which, substantially, only contains water, and a concentrate of lactic acid as a third retentate R3.

2. The process of claim 1, wherein acid whey having a lactic acid content in the range of about 0.1 to 1% by weight is used.

3. The process of claim 1, wherein the second nanofiltration step is performed using a membrane having a lower cut-off than the membrane of the first nanofiltration step.

4. The process of claim 1, wherein the first nanofiltration step is performed at a pressure in the range of about 10 to about 15 bar.

5. The process of claim 1, wherein the second nanofiltration step is performed using a closed membrane.

6. The process of claim 5, wherein a closed nanofiltration membrane having a cut-off in the range of about 150 to about 300 Dalton is used.

7. The process of claim 1, wherein the second nanofiltration step is performed at a pressure in the range of about 30 to about 40 bar.

8. The process of claim 1, wherein the lactic acid concentrate is subsequently dehydrated.

* * * * *